United States Patent [19]

Hylarides et al.

[11] Patent Number: 5,563,250

[45] Date of Patent: Oct. 8, 1996

[54] CLEAVABLE CONJUGATES FOR THE DELIVERY AND RELEASE OF AGENTS IN NATIVE FORM

[75] Inventors: Mark D. Hylarides, Snohomish County; Ananthachari Srinivasan; Jeffrey N. Fitzner, both of King County; Vivekananda M. Vrudhula, Snohomish County, all of Wash.

[73] Assignee: NeoRx Corporation, Seattle, Wash.

[21] Appl. No.: 242,702

[22] Filed: May 13, 1994

Related U.S. Application Data

[60] Continuation of Ser. No. 915,004, Jul. 16, 1992, abandoned, which is a division of Ser. No. 678,535, Mar. 29, 1991, Pat. No. 5,141,648, which is a division of Ser. No. 454,295, Dec. 19, 1989, Pat. No. 5,017,693, which is a continuation-in-part of Ser. No. 362,355, Jun. 6, 1989, abandoned, and a continuation-in-part of Ser. No. 127,656, Dec. 2, 1987, abandoned.

[51] Int. Cl.$^6$ .............................. C07H 3/02; C07H 5/02; C07H 5/04; C07D 207/04; C07D 295/04; C07D 307/12; C07D 307/14; C07D 333/00

[52] U.S. Cl. ........................ 536/4.1; 536/6; 536/6.1; 536/6.2; 536/17.2; 536/17.3; 536/17.5; 536/18.2; 536/18.3; 536/18.4; 536/18.7; 536/22.1; 536/53; 536/54; 536/115; 536/122; 546/243; 546/244; 546/246; 546/248; 548/543; 548/550; 548/551; 548/558; 549/28; 549/62; 549/65; 549/68; 549/72; 549/73; 549/416; 549/417; 549/419; 549/476; 549/480; 549/491; 549/497

[58] Field of Search ...................... 536/4.1, 6, 6.1, 536/6.2, 17.2, 17.3, 17.5, 18.2, 18.3, 18.4, 18.7, 22.1, 53, 54, 115, 118, 119, 120, 122; 549/476, 480, 417, 416, 419, 28, 62, 65, 68, 72, 73, 491, 497; 546/243, 244, 246, 248; 548/543, 501, 551, 558

[56] References Cited

U.S. PATENT DOCUMENTS

| | | | |
|---|---|---|---|
| 4,489,710 | 12/1984 | Spitler | 128/898 |
| 4,507,234 | 3/1985 | Kato et al. | 530/363 |
| 4,511,501 | 4/1985 | Luduena | 530/408 |
| 4,542,225 | 9/1985 | Blattler et al. | 548/473 |
| 4,569,789 | 2/1986 | Blattler et al. | 530/391.9 |
| 4,618,492 | 10/1986 | Blattler et al. | 424/85.91 |
| 4,625,014 | 11/1986 | Senter et al. | 530/300 |
| 4,638,045 | 11/1987 | Kohn et al. | 530/323 |
| 4,671,958 | 6/1987 | Rodwell et al. | 424/86 |
| 4,689,311 | 8/1987 | Weltman | 436/519 |
| 4,851,423 | 7/1989 | Girijavallabhan et al. | 514/399 |
| 4,943,636 | 7/1990 | Nitecki et al. | 546/294 |
| 4,963,355 | 10/1990 | Kim et al. | 424/85.8 |
| 5,017,693 | 5/1991 | Hylarides et al. | 530/391.1 |
| 5,032,518 | 7/1991 | Huber et al. | 435/178 |
| 5,093,475 | 3/1992 | Carroll et al. | 530/391.9 |
| 5,141,648 | 8/1992 | Hylarides et al. | 210/635 |

OTHER PUBLICATIONS

Banthrope et al (1979) Phytochemistry 18:666–667.
Elbein (1984) CRC Crit. Rev. Biochem. 16(1):21–49.
Amarnath et al (1977) Chemical Rev. 77(2):183–217.
Kennedy et al (1976) Clin. Chim. Acta 70:1–31.
Blair et al (1983) J. Immunol. Methods 59:129–143.
Banthorpe et al. "On the Structure of a Novel Ether From *Artemisia Tridentata*", *Phytochemistry* 18:666–667 (1979).
Duncan et al., "A New Reagent Which May Be Used to Introduce Sulfhydryl Groups into Proteins, and Its Use in the Preparation of Conugates for Immunoassay," *Anal. Biochem.* 132:68–73 (1983).
de Duve, "Lysomsomes Revisted," *Eur. J. Biochem.* 137:391–397 (1983).
Aplin et al (1981) "Preparation, Properties, and Applications of Carbohydrate Ponjugates of Proteins and Lipids" CRC Crit. Rev. Biochem. 10:259–306.

*Primary Examiner*—Kay K. A. Kim
*Attorney, Agent, or Firm*—Seed and Berry LLP

[57] ABSTRACT

The present invention provides cleavable conjugates whose linkers contain a labile bond that is cleavable under a variety of mild conditions, including weakly acidic. Since the agent may be bonded directly to the linker, cleavage can result in release of native agent. The invention also provides methods for producing cleavable conjugates. Preferred agents include drugs, toxins, biological response modifiers, radiodiagnostic compounds, radiotherapeutic compounds, and derivatives thereof. The targeting molecule employed in the invention may be an intact molecule, a fragment thereof, or a functional equivalent thereof. In a particularly preferred embodiment, the targeting molecule is a monoclonal antibody directed towards a tumor-associated antigen in man. The invention further provides methods for delivering to the cytoplasm of a target cell an agent free of its targeting molecule carrier. A diagnostically/therapeutically effective dose of a cleavable conjugate is administered to a warm-blooded animal such as man.

3 Claims, No Drawings

CLEAVABLE CONJUGATES FOR THE DELIVERY AND RELEASE OF AGENTS IN NATIVE FORM

CROSS REFERENCE TO RELATED APPLICATION

This application is a continuation of U.S. patent application Ser. No. 07/915,004, filed Jul. 16, 1992 now abandoned; which is a division of Ser. No. 07/678,535, filed Mar. 29, 1991, now U.S. Pat. No. 5,141,648, which is a division of Ser. No. 07/454,295, filed Dec. 19, 1989, issued as U.S. Pat. No. 5,017,693; which is a continuation-in-part application to Ser. No. 07/362,355, filed Jun. 6, 1989, abandoned, and Ser. No. 07/127,656, filed Dec. 2, 1987, abandoned.

TECHNICAL FIELD

The present invention relates generally to cleavable conjugates that permit release of an agent in native form under mild conditions and to methods for making and using these conjugates.

BACKGROUND OF THE INVENTION

A reoccurring problem in medicine is that, due to the lack of specificity of the agents used for treatment of illnesses, the patient is often the recipient of a new set of maladies from the therapy. This scenario is common especially in the treatment of the various forms of cancer.

An approach taken to circumvent the nonspecificity of the agents used to treat diseases is to couple an agent to a carrier that possesses some degree of specificity. A number of molecules have been utilized as carriers in agent delivery systems, but with limited success. Carrier molecules such as liposomes, proteins, and polyclonal antibodies have been used in conjunction with a broad spectrum of pharmaceutical or cytotoxic agents including radioactive compounds, agents which bind DNA, antimetabolites, agents which act on cell surfaces, and protein synthesis inhibitors.

With the discovery of a method to isolate antibodies with a single specificity, i.e., monoclonal antibodies (MAbs), came the hope that agents could now be delivered to selected cells via "immunoconjugates." "Immunoconjugates" are covalently bonded hybrid molecules composed of a recognition portion, such as an antibody molecule, an antibody fragment, or a functional equivalent thereof, and a biologically active portion, such as a toxin, toxin fragment, a drug, a biological response modifier, or a radioisotope. Immunoconjugates have enormous potential as potent anti-tumor agents, due to the selectivity imparted to the hybrid molecules by the antibody portion of the immunoconjugate. The exquisite selectivity of antibodies or antibody fragments permits delivery of increased dose of cytotoxic, inhibitory or radiolabled moieties to a defined population of cells.

Although the MAb carrier systems have gone far to solve the cell-specificity problem, other problems remain. In particular, the design of the compound used to link the agent to the MAb is important. First, where the agent is only active, or at least more potent, when free from the MAb carrier, the linker needs to be cleavable in order to release the agent. Second, where the agent is only active, or at least more potent, when none of the linker remains attached following the cleavage, the labile bond must be the one formed between the linker and the agent. Third, the type of labile bond used should be chosen on the basis of the location, i.e., inside or outside of a cell, of the release-inducing factor.

A number of different cleavable linker groups have been described previously. The mechanisms for release of an agent from these linker groups include cleavage by reduction of a disulfide bond, by irradiation of a photolabile bond, by hydrolysis of derivatized amino acid side chain, by serum complement-mediated hydrolysis, and acid-catalyzed hydrolysis. Some of these mechanisms are susceptible to release of the agent prior to having reached the specific cell, tissue or organ. Other of these mechanisms will provide faithful external delivery, however, they are inappropriate where the actual target site of the agent is inside a cell. Where an agent activates or inactivates a cell by binding to an intracellular component, the carrier-agent conjugate must be internalized and then the agent released.

A way to achieve internalization of a carrier-agent conjugate is to take advantage of a cell's receptor-mediated endocytosis pathway. Antibodies are one example of a carrier that will bind to cell surface receptors and be internalized. Receptors which are internalized by receptor-mediated endocytosis pass through acidified compartments known as endosomes or receptosomes. Thus, the carrier-agent conjugate will be exposed transiently to an acidic pH.

Blattler et al., in U.S. Pat. No. 4,569,789, describe a drug delivery system which is formed by reaction of an active substance with a maleic anhydride moiety. The active substance is released upon cleavage of the amide bond. The patent purports that cleavage occurs under mildly acidic conditions, yet the patent discloses that at pH 5 only about 15% is cleaved after five hours. Even at pH 4 for five hours, less than 50% is cleaved.

Thus, there is a need in the art for a carrier-agent conjugate which releases the agent by cleavage under mild conditions. The present invention fulfills this need and further provides other related advantages.

SUMMARY OF THE INVENTION

Briefly stated, the present invention, in one aspect, provides for a method of producing cleavable immunoconjugates comprising the steps of reacting an agent with a compound having the formula (I):

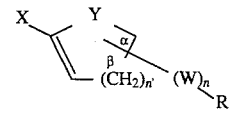

where:

R is a chemically reactive moiety;

W is a methylene, methylenoxy, or methylenecarbonyl group or combination thereof;

n is 0 to 10

Y is an O, S, or NR', wherein R' is an alkyl group of $C_6$ or less;

n' is 1 to 2; and

X is an H, alkyl group of $C_6$ or less, or alkoxy group of $C_6$ or less.

The agent adds to the carbon-carbon double bond, thereby forming a derivatized agent. The derivatized agent is conjugated with an antibody or antibody fragment for delivery to a cell, thereby forming the cleavable immunoconjugate. A variation on this method is to reverse the order of addition of an agent to the compound and of conjugation of an antibody.

In another aspect, the invention provides a clearable immunoconjugate. The immunoconjugate has the formula (II):

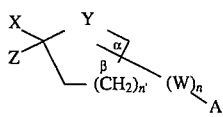

where:
- A is an antibody including the linking function, or antibody fragment including the linking function;
- W is methylene, methylenoxy, or methylenecarbonyl group or combination thereof;
- n is 0 to 10;
- Y is an O, S or NR', wherein R' is an alkyl group of $C_6$ or less;
- n' is 1 to 2;
- X is H, alkyl group of $C_6$ or less, or alkoxy group of $C_6$ or less; and
- Z is an agent.

In yet another aspect, the present invention provides a method for delivering to the cytoplasm of a target cell an agent free of its antibody carrier. The method comprises the step of administering to a mammal a diagnostically or therapeutically effective dose of a cleavable immunoconjugate having the formula (II):

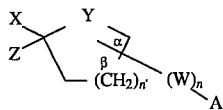

where:
- A is an antibody including the linking function, or an antibody fragment including the linking function;
- W is methylene, methylenoxy, or methylenecarbonyl group or combination thereof;
- n is 0 to 10
- Y is an O, S or NR' wherein R' is an alkyl group of $C_6$ or less;
- n' is 1 to 2;
- X is H, alkyl group of $C_6$ or less, or alkoxy group of $C_6$ or less; and
- Z is a diagnostically or therapeutically effective agent.

Upon delivery of the immunoconjugate to a target cell, cleavage occurs at the bond between the agent and the compound linking the agent to the antibody, thereby releasing the agent. The bond is cleavable under a variety of conditions, inducing mildly acidic conditions or divalent cations, and is accelerated by heat. Since the agent may be bonded via one of its nucleophilic groups directly to the linker, cleavage can result in release of native agent.

A related aspect of the present invention provides a method for isolating a compound. The method comprises the steps of conjugating to a solid phase a reagent having the formula (I):

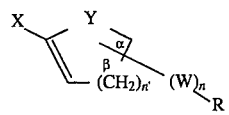

where:
- R is a chemically reactive moiety;
- W is a methylene, methylenoxy, or methylenecarbonyl group or combinations thereof;
- n is 0 to 30;
- Y is an O, S or NR', wherein R' is an alkyl group of $C_6$ or less;
- n' is 1 to 2; and
- X is an H, alkyl group of $C_6$ or less, or alkoxy group of $C_6$ or less.

Thus, a derivatized solid phase is formed. The derivatized solid phase is contacted with a sample solution in which a compound containing an available nucleophilic group is present. The compound binds to the derivatized solid phase, thereby removing the compound from the sample solution. The bound compound is released from the derivatized solid phase by a variety of conditions, including mildly acidic conditions or divalent cations, and heat accelerates the reaction.

In yet another aspect, the present invention provides a method for introducing into a compound a free sulfhydryl, free amino, or free hydroxyl group. The method comprises the steps of reacting a compound with a reagent having the formula (V):

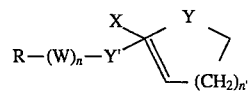

where:
- R is a chemically reactive moiety;
- W is a methylene, methylenoxy, or methylenecarbonyl group or combinations thereof;
- n is 0 to 30;
- Y' is S, O, or N;
- X is H, alkyl group of $C_6$ or less, or alkoxy group of $C_6$ or less;
- n' is 1 to 2; and
- Y is an O, S or NR' wherein R' is an alkyl group of $C_6$ or less;

to form a reagent-linked compound. The reagent-linked compound is cleaved at the bond between Y' and the ring. Depending upon whether Y' is an S, O, or N, a free sulfhydryl, free hydroxyl, or free amino group, respectively, will be added to the compound. The cleavage occurs under a variety of conditions, including mildly acidic conditions or divalent cations, and heat accelerates the reaction.

The invention in another aspect provides additional cleavable conjugates. The conjugates have the formula (III):

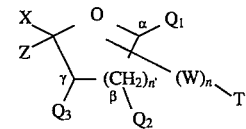

where:
- T is a targeting molecule;
- W is a methylene, methylenoxy, or methylenecarbonyl group or combinations thereof;
- n is 0 to 10;
- $Q_1$, $Q_2$ and $Q_3$ are independently selected from H, OH, O-alkyl, O-acyl, and derivatives thereof, with the proviso that $Q_1$, $Q_2$ and $Q_3$ are not all H;
- n' is 1 to 2;
- X is an H, alkyl group of $C_6$ or less, or alkoxy group of $C_6$ or less; and
- Z is an agent.

In another aspect, the present invention provides an additional method for delivering to the cytoplasm of a target cell an agent free of its targeting molecule carrier. The method comprises the step of administering to a warm-blooded animal a diagnostically or therapeutically effective does of a cleavable conjugate having the formula (III):

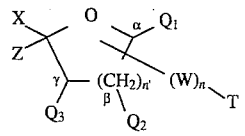

where:

T is a targeting molecule;

W is a methylene, methylenoxy, or methylenecarbonyl group or combinations thereof;

n is 0 to 10;

$Q_1$, $Q_2$ and $Q_3$ are independently selected from H, OH, O-alkyl, O-acyl, and derivatives thereof, with the proviso that $Q_1$, $Q_2$ and $Q_3$ are not all H;

n' is 1 to 2;

X is an H, alkyl group of $C_6$ or less, or alkoxy group of $C_6$ or less; and

Z is a diagnostically or therapeutically effective agent.

Upon delivery of the conjugate to a target cell, cleavage occurs at the bond between the agent and the compound inking the agent to the targeting molecule, thereby releasing the agent. The bond is cleavable under a variety of conditions, including mildly acidic conditions, and is accelerated by heat. Since the agent may be bonded directly to the linker, cleavage can result in release of native agent.

A related aspect of the present invention provides another method for isolating a compound. The method comprises the steps of conjugating to a solid phase, via R, a reagent having the formula (IV):

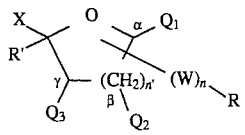

where:

R' is a chemically reactive group;

W is a methylene, methylenoxy, or methylenecarbonyl group or combinations thereof;

n is 0 to 30;

$Q_1$, $Q_2$ and $Q_3$ are independently selected from H, OH, O-alkyl, O-acyl, and derivatives thereof, with the proviso that $Q_1$, $Q_2$ and $Q_3$ are not all H;

n' is 1 to 2;

X is an H, alkyl group of $C_6$ or less, or alkoxy group of $C_6$ or less; and

R is a chemically reactive group, with the provisos that R is attached directly or indirectly to one of the carbons designated α, β or γ, that when R is attached to α then $Q_1$ is H, that when R is attached to β then $Q_2$ is H, that when R is attached to γ then $Q_3$ is H, and that R and R' are not the same.

Thus, a derivatized solid phase is formed. The derivatized solid phase is contacted with a sample solution in which a compound containing a group capable of reacting with R' is present. The compound binds to the derivatized solid phase, thereby removing the compound from the sample solution.

The bound compound is released from the derivatized solid phase by a variety of conditions, including mildly acidic conditions, and heat accelerates the reaction.

In yet another aspect, the present invention provides an additional method for introducing into a compound a free sulfhydryl, free amino, or free hydroxyl group. The method comprises the steps of reacting a compound with a reagent having the formula (VI):

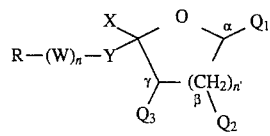

where:

R is a chemically reactive group;

W is a methylene, methylenoxy, or methylenecarbonyl group or combinations thereof;

n is 0 to 30;

Y is S, N, or O;

X is H, alkyl group of $C_6$ or less, or alkoxy group of $C_6$ or less;

n' is 1 to 2; and $Q_1$, $Q_2$ and $Q_3$ are independently selected from H, OH, O-alkyl, O-acyl, and derivatives thereof, with the proviso that $Q_1$, $Q_2$ and $Q_3$ are not all H;

to form a reagent-linked compound. The reagent-linked compound is cleaved at the bond between Y and the ring. Depending upon whether Y is an S, O, or N, a free sulfhydryl, free hydroxyl, or free amino group, respectively, will be added to the compound. The cleavage occurs under a variety of conditions including mildly acidic conditions, and heat accelerates the reaction.

Other aspects of the invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

Targeting molecule—any molecule, i.e., a protein or a non-protein, that has the capacity to bind to a defined population of cells; and may be an intact molecule, a fragment thereof, or a functional equivalent thereof; and may be genetically engineered.

Protein—as used herein, includes proteins, polypeptides, and peptides; and may be an intact molecule, a fragment thereof, or a functional equivalent thereof; and may be genetically engineered; an example is an antibody.

Antibody—as used herein, includes both polyclonal and monoclonal antibodies; examples of antibody fragments include F(ab')$_2$, Fab', Fab and Fv.

As noted above, the present invention provides cleavable conjugates. One advantage of the conjugates provided herein is that cleavage occurs under mildly acidic conditions. For example, subjecting a conjugate to pH 5 results in substantially complete cleavage. The release mechanism may proceed as follows. An equivalent of acid is thought to initially protonate the ring O. This is followed by formation of a stable carbocation. A second equivalent of acid results in the release of the agent and the formation of an aldehyde or ketone on the compound linking the agent to the targeting molecule.

Another advantage of the conjugates of the present invention is that cleavage results in the release of the agent without any of the linker remaining attached. Popular cleavable linkers are those bifunctional reagents with a disulfide bond interposed between two reactive end groups. Cleavage of the disulfide bond by the addition of a reducing compound leaves one end of the bifunctional reagent still attached to the agent. Many agents, however, are inactivated by the permanent addition of a linker or fragment thereof to their structures. The conjugates of the present invention are cleaved at the bond formed between the agent and the compound linking the agent to the targeting molecule. Therefore, the present invention provides a way of releasing an agent in native form at the target site.

Yet another advantage of the present invention is the ease of preparation of the linking compound, due in part to the commercial availability of the reagents needed.

Conjugates in which one of the components is a targeting molecule have enormous potential as potent anti-tumor agents. This is due to the selectivity imparted to the conjugate by the targeting molecule portion. The exquisite selectivity of antibodies, for example, permits delivery of increased doses of agents, such as those that are cytotoxic, inhibitory, radiolabeled, or biological response modifiers.

A targeting molecule has the capacity to bind to a defined population of cells. The targeting molecule may bind through a receptor, substrate, antigenic determinant, or other binding site on the target cell population. Preferred targeting molecules useful within the present invention include antibodies; peptides, such as bombesin, gastrin-releasing peptide, RDG peptide, substance P, neuromedin-B, neuromedin-C, and metenkephalin; and hormones, such as estradiol, neurotensin, melanocyte-stimulating hormone, foilice-stimulating hormone, lutenizing hormone, and human growth hormone. Other suitable targeting molecules include serum proteins, fibrinolytic enzymes, and biological response modifiers, such as interleukin, interferon, erythropoietin and colony-stimulating factor. Analogs of the above-listed targeting molecules that retain the ability to bind to the defined target cell population may also be used within the present invention. In addition, synthetic targeting proteins and peptides may be designed and made to "fit" a particular characterized epitope (binding site). That is, a synthetic targeting protein/peptide would be designed to bind a specific epitope in a "lock and key" fashion. Within the present invention, antibodies, bombesin and gastrin-releasing peptide and their analogs are particularly preferred targeting molecules.

When an antibody is employed in the present invention, it may be an intact molecule, a fragment thereof, or a functional equivalent thereof. Examples of antibody fragments are F(ab')$_2$, Fab', and Fv. While polyclonal antibodies may be employed in the present invention, monoclonal antibodies (MAbs) are preferred, especially those directed toward a tumor-associated antigen in man. Particularly preferred MAbs are anti-TAC, or other interleukin 2 receptor antibodies; 9.2.27 and NR-ML-05 to human melanoma associated proteoglycan; NR-Lr-10 to 37–40 kilodalton pancarcinoma glycoprotein and OVB$_3$ to an as yet unidentified antigen. Genetically engineered antibodies or fragments thereof of these and other MAbs may be employed as well.

Within the present invention, monoclonal antibodies were prepared by immunizing rodents or other animals and/or are developed by harvesting human lymphocytes from patients bearing malignancies and immortalizing the antibody secretion of the cells by standard hybridoma technology (e.g., Geffer et al., *Somatic Cell Genet.* 3:231, 1977). Alternatively, polyclonal antiserum is prepared by harvesting serum from animals following immunization with tumor cells or other defined tumor-associated antigens or harvesting from humans who have or have had exposure to tumors or tumor-associated antigens, and subjecting the serum to standard purification techniques. Antibodies were screened for specificity using a standard radioimmunoassay or an enzyme-linked immunosorbent assay (ELISA) against the appropriate targets. Screening was performed with normal human tissues to select antibody with appropriate tumor specificity.

Agents suitable within the present invention include drugs, toxins, biological response modifiers, radiodiagnostic compounds and radiotherapeutic compounds. Preferred drugs include cancer chemotherapeutic agents. Preferred toxins include bacterial exotoxins and plant toxins. Particularly preferred toxins include ricin, abrin, diphtheria toxin, cholera toxin, gelonin, pokeweed antiviral protein, tritin, Shigella toxin, and Pseudomonas exotoxin A. Preferred radionuclides for the radiodiagnostic and radiotherapeutic compounds include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212.

As noted above, the present invention provides a method for producing a cleavable conjugate comprising the steps of reacting an agent, capable of addition to a carbon-carbon double bond, with a compound having the formula (I):

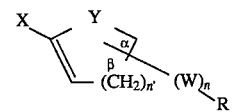

to form a derivatized agent and conjugating the derivatized agent with a targeting molecule, such as an antibody or fragment thereof, to form the cleavable conjugate.

The elements of the compound depicted above in formula I include the following. R is a chemically reactive moiety. The moiety may be strongly electrophilic or nucleophilic and thereby be available for reacting directly with, for example, an antibody or fragment thereof. Alternatively, the moiety may be a weaker electrophile or nucleophile and therefore require activation prior to the conjugation with an antibody or fragment thereof. This alternative would be desirable where it is necessary to delay activation of R until an agent is added to the compound in order to prevent the reaction of the agent with R. In either scenario R is chemically reactive, the scenarios differ by whether following addition of an agent, R is reacted directly with an antibody or fragment thereof or is reacted first with one or more chemicals to render R capable of reacting with an antibody or fragment thereof. A discussion of reactions illustrative of the activation of R is found below.

W in formula I is a group that functions as a "spacer arm" and may be useful to distance the antibody or fragment thereof from the agent. Groups which may be used include methylene (—CH$_2$—), methyleneoxy (—CH$_2$—O—), methylenecarbonyl (—CH$_2$—CO—), amino acids, or combinations thereof. The number, n, of groups such as these would be typically 0 to 30 and preferably 0 to 10. W, or R where n is 0, may be attached to one or the other of the ring positions designated as α and β. Because the number of methylene ring carbons at the β position is defined by n' which may be greater than one, the β position includes additional points for attachment of a W or an R to the ring.

Y in the formula I is a heteroatom. Preferred heteroatoms include oxygen (O), sulfur (S), or nitrogen (N). When nitrogen is the heteroatom, it should be in the form of a tertiary amine, i.e., NR', such as where R' is an alkyl group of $C_6$ or less. A particularly preferred heteroatom is O. The ring size of the compound may be increased above 5 by an increase in the number, n', of ring methylene groups. Preferred are 5-membered rings, such as a dihydrofuran derivative, and 6-membered rings. X may be a hydrogen (H) or another substituent, preferably an alkyl group of $C_6$ or less and an alkoxy group of $C_6$ or less.

The step of reacting an agent and a compound of formula I results in the attachment of the agent to the compound via addition to the carbon-carbon double bond on the ring. In this manner, a derivatized agent is formed. Any agent containing a group capable of reacting with the compound may be employed in the present invention. Preferred agents include drugs, toxins, biological response modifiers, radiodiagnostic compounds and radiotherapeutic compounds. An agent may be reacted in its native form or a derivative thereof. An example of a derivative form is where an amino group on an agent is modified by reaction with a compound, such as iminothiolane, to introduce a sulfhydryl group on the agent. Particularly preferred toxins include ricin, abrin, diphtheria toxin and Pseudomonas exotoxin A. Particularly preferred radionuclides for the radiodiagnostic and radiotherapeutic compounds include $^{99m}Tc$, $^{186/188}Re$, and $^{123/131}I$.

The step of conjugating may be performed by joining an antibody or fragment thereof to the derivatized agent by direct reaction with R. Alternatively, it may be desirable to include before the step of conjugation a preparatory step. For example, an antibody or fragment thereof may be itself derivatized in preparation for direct reaction with R. The derivatization of an antibody or antibody fragment includes reaction with any of the numerous bifunctional reagents reported in the literature.

A direct reaction with R by derivatized or underivatized antibody or fragment thereof is intended to mean that R is capable of reacting with the derivatized or underivatized antibody or fragment. For example, R may be a carbonyl-containing group, such as an anhydride or an acid halide, or an alkyl group containing a good leaving group, e.g., a halide. The latter class of compounds may be represented by alkyl X', where X' stands for the leaving group. As another example, R may be a nucleophilic group, such as an amino or sulfhydryl group, which is capable of reacting with a derivatized antibody or fragment, e.g., containing a maleimide group.

Yet another way to perform a step in preparation for conjugation of the derivatized agent with underivatized or derivatized antibody or antibody fragment is to convert R. Examples of conversions of R include where R is a carboxyl group and is then activated. Activation of a carboxyl group includes formation of an "active ester," such as a succinimidyl ester. The term "active ester" is known to refer to esters which are highly reactive in nucleophilic substitution reactions. In the present invention, the antibody fragment would be the nucleophile.

Another example of a conversion is where R is a succinimide derivative containing a protective group, such as phenylsulfonyl. Upon removal of the group, the succinimide is converted to a maleimide which is highly reactive in nucleophilic addition reactions. Alternatively, R may be an amino, sulfhydryl, or hydroxyl group and the conversion comprises reaction with a bifunctional reagent. It will be evident to one skilled in the art that a variety of bifunctional reagents, both homobifunctional and heterobifunctional, may be employed within the present invention.

A variation on this method is to reverse the order of the addition of an agent and an antibody in the formation of an immunoconjugate. Specifically, first an antibody is conjugated to a compound, whose general structure is depicted above, via R and then an agent is reacted via addition to the double bond on the compound attached to the antibody. The above discussion regarding the compound, agent, antibody, and chemical reactions is relevant to this variation as well.

In a related aspect, the present invention provides cleavable conjugates having the formula (II):

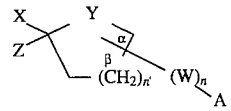

where: W, n, Y, n', α, β, and X are defined as described above for formula I. A is a targeting molecule, such as an antibody or an antibody fragment, and it includes any linking function used to attach, for example, an antibody or fragment to yield an immunoconjugate. Preferred targeting molecules are described above.

Z is an agent. Any agent capable of being covalently attached to the cleavable conjugate may be employed in the present invention. Typically, an agent will be bonded to the conjugate by use of a sulfhydryl, amino, or hydroxyl group on the agent. The agent may be bonded directly to the conjugate or indirectly with a linking function interposed between the agent and the ring. Preferred agents include those described above.

An additional aspect of the present invention provides a method for delivering to the cytoplasm of a target cell an agent free of its antibody carrier. The method comprises the step of administering to a mammal a diagnostically or therapeutically effective dose of a cleavable conjugate having the formula (II):

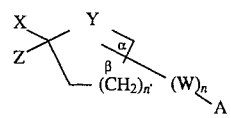

where W, n, Y, n', α, β, X, A, and Z are defined above A preferred mammal is man. Preferred targeting molecules and agents include those described above.

The agent may be diagnostically and/or therapeutically effective. A particularly preferred diagnostic agent is a compound containing $^{99m}Tc$. A diagnostically effective dose of a cleavable immunoconjugate incorporating such an agent is generally from about 10 to about 30, typically from about 15 to about 25, and preferably from about 18 to about 20 mCi per 75 kg body weight. A preferred therapeutic agent is a toxin, such as Pseudomonas exotoxin A. A therapeutically effective dose of a cleavable immunoconjugate incorporating such an agent is generally from about 1 to about 100 and preferably from about 1 to 10 ng per 75 kg body weight. The precise dose for a particular cleavable immunoconjugate is dependent upon the antibody used, as antibodies vary with respect to the number of receptors and their affinity for the receptors, and the agent(s) used, as toxins, for example, vary (varies) with respect to their potency. It will be evident to one skilled in the art how to determine the optimal effective dose for a particular cleavable immunoconjugate.

The step of administering to a mammal a diagnostically or therapeutically effective dose of a cleavable immunoconjugate having formula II sets in motion a sequence of events in vivo that results in the agent portion of the immunoconjugate being delivered free of the antibody portion of the cytoplasm of a target cell. The antibody or antibody fragment portion of the immunoconjugate imparts the selectivity which permits delivery to and binding at the surface of a specific cell. An immunoconjugate of formula II is susceptible to cleavage for pH less than or equal to 6.0 and the acid-catalyzed cleavage is accelerated by heating above room temperature, about 23°. Since antibodies bind to cell surface receptors which are internalized into the cytoplasm via acidified compartments, it is believed that the release to the cytoplasm of an agent from an immunoconjugate of the type described herein is the result of this transient exposure to acidic pH. Further, because mammals such as man have normal body temperatures above 23° C., body heat may be a factor in the release. The delivery of an agent free of its antibody carrier to the cytoplasm of a targeted cell increases its potency as compared to the agent when irreversibly linked to its carrier. This method is useful to diagnose, stage, evaluate or treat diseases such as cancer in humans.

As noted above, another aspect of the present invention provides clearable conjugates having the formula (III):

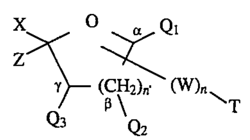

The elements of the conjugate depicted in formula III include the following. W is a group that functions as a "spacer arm" and may be useful to distance the targeting molecule from the agent. Groups which may be used include methylene ($—CH_2—$), methyleneoxy ($—CH_2—O$), methylenecarbonyl ($—CH_2—CO—$), amino acids, or combinations thereof. The number, n, of groups such as these would be typically 0 to 30 and preferably 0 to 10. W, or T where n is 0, may be attached to one of the ring positions designated as α, β, and γ. Because the number of methylene ring carbons at the β position is defined by n', which may be greater than one, the β position includes additional points for attachment of a W or a T to the ring.

$Q_1$, $Q_2$ and $Q_3$ are independently selected from H, OH, O-alkyl, O-acyl, and derivatives thereof. The ring size of the compound may be increased above 5 by an increase in the number, n', of ring methylene groups Preferred are 5-membered rings and 6-membered rings. X may be a hydrogen (H) or another substituent, preferably an alkyl group of $C_6$ or less or an alkoxy group of $C_6$ or less.

Z is an agent. Preferred agents include those described above. Particularly preferred are radiodiagnostic and radiotherapeutic compounds.

T is a targeting molecule, and, as used herein, includes a chemical group or groups ("linking function"), if any, used to attach the targeting molecule to form a conjugate. That is, a targeting molecule may be bonded to W directly or via a linking function, or when n is 0, it may be bonded to a ring-carbon directly or via a linking function. It will be evident to one skilled in the art that a variety of linking functions may be employed within the present invention and examples are described below. Preferred targeting molecules include those described above.

The conjugates of formula III may be produced by a variety of methods. For example, a targeting molecule and an agent may be conjugated to a compound having the formula (IV):

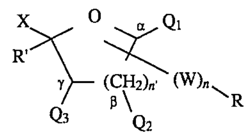

where W, n, $Q_{1-3}$, n', and X are defined as described above for formula III. R and R' are chemically reactive groups. R is attached indirectly, or directly when n is 0, to one of the carbons designated α, β, or γ. A targeting molecule is conjugated to the compound via R and an agent via R'. Generally, R and R' are not the same.

R is a chemically reactive group. The group may be strongly electrophilic or nucleophilic and thereby be available for reacting directly with a targeting molecule. Alternatively, the group may be a weaker electrophile or nucleophile and therefore require activation prior to the conjugation with a targeting molecule. This alternative would be desirable where it is necessary to delay activation of R until an agent is conjugated to the compound in order to prevent the reaction of the agent with R. In either scenario, R is chemically reactive. The scenarios differ by whether following addition of an agent, R is reacted directly with a targeting molecule or is reacted first with one or more chemicals to render R capable of reacting with a targeting molecule. A discussion of reactions illustrative of the activation of R is found below.

The step of conjugating a targeting molecule may be performed by joining the targeting molecule by direct reaction with R. Alternatively, it may be desirable to include before the step of conjugation a preparatory step. For example, a targeting molecule may be itself derivatized in preparation for direct reaction with R. The derivatization of a targeting molecule includes reaction with any of the numerous bifunctional reagents reported in the literature. An example of a derivative form is where an amino group on a targeting agent is modified by reaction with a reagent, such as iminothiolane, to introduce a sulfhydryl group on the targeting molecule.

A direct reaction with R by a derivatized or underivatized targeting molecule is intended to mean that R is capable of reacting with the derivatized or underivatized targeting molecule. For example, R may be a carbonyl-containing group, such as an anhydride or an acid halide, or an alkyl group containing a good leaving group, e.g., a halide. The latter class of compounds may be represented by alkyl X', where X' stands for the leaving group. As another example, R may be a nucleophilic group, such as an amino or sulfhydryl group, which is capable of reacting with a derivatized targeting molecule, e.g., containing a maleimide group.

Yet another way to perform a step in preparation for conjugation of an underivatized or derivatized targeting molecule is to convert R. Examples of conversions of R include where R is a carboxyl group and is then activated. Activation of a carboxyl group includes formation of an "active ester," such as a succinimidyl ester. The term "active ester" is known to refer to esters which are highly reactive in nucleophilic substitution reactions. In the present invention, the targeting molecule would be the nucleophile.

Another example of a conversion is where R is a succinimide derivative containing a protective group, such as phenylsulfonyl. Upon removal of the group, the succinimide is converted to a maleimide which is highly reactive in nucleophilic addition reactions. Alternatively, R may be an amino, sulfhydryl, or hydroxyl group and the conversion comprises reaction with a bifunctional reagent. It will be evident to one skilled in the art that a variety of bifunctional reagents, both homobifunctional and heterobifunctional, may be employed within the present invention.

The above discussion regarding R is applicable to the other chemically reactive group, R', on the compound (IV). As with the targeting molecule, an agent may be reacted in its native form or derivatized in preparation for reaction with R'. The selection of certain chemically reactive groups, e.g., Br or $OCH_3$, for R' permits the attachment of an agent directly, e.g., via an amino group on the agent, to the ring. Consequently, cleavage of such conjugates results in the release of the agent without any of the compound remaining attached.

Instead of attaching an agent first and a targeting molecule second in the formation of a conjugate, the order may be reversed. Specifically, first a targeting molecule is conjugated to a compound, whose structure (IV) is depicted above, via R, and then an agent is reacted via R' on the compound attached to the targeting molecule. The above discussion regarding the compound, agent, targeting molecule, and chemical reactions is relevant to this variation as well.

An additional aspect of the present invention provides a method for delivering to the cytoplasm of a target cell an agent free of its targeting molecule carrier. The method comprises the step of administering to a warm-blooded animal a diagnostically or therapeutically effective dose of a cleavable immunoconjugate having the formula (III):

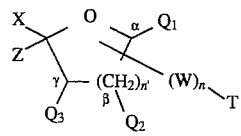

where W, n, $Q_{1-3}$, n', $\alpha$, $\beta$, $\gamma$, X, T, and Z are defined above. A preferred warm-blooded animal is man. Preferred targeting molecules and agents include those described above.

The agent may be diagnostically and/or therapeutically effective. Preferred agents include those described above. A particularly preferred diagnostic agent is a compound containing $99m_{Tc}$. A diagnostically effective dose of a cleavable conjugate incorporating such an agent is generally from about 10 to about 30, typically from about 15 to about 25, and preferably from about 18 to 20 mCi per 75 kg body weight. A particularly preferred therapeutic agent is a drug or toxin, such as Pseudomonas exotoxin A. A therapeutically effective dose of a cleavable conjugate incorporating such a toxin agent is generally from about 1 to about 100 and preferably from about 1 to about 10 ng per 75 kg of body weight. The precise dose for a particular cleavable conjugate is dependent upon the targeting molecule used, e.g., antibodies vary with respect to the number of receptors and their affinity for the receptors, and the agent used, e.g., toxins vary with respect to their potency. It will be evident to one skilled in the art how to determine the optimal effective dose for a particular cleavable conjugate.

The step of administering to a warm-blooded animal a diagnostically or therapeutically effective dose of a cleavable conjugate having formula III sets in motion a sequence of events in vivo that results in the agent portion of a conjugate being delivered free of the targeting molecule portion to the cytoplasm of a target cell. The targeting molecule of the conjugate imparts the selectivity which permits delivery to and binding at the surface of a specific cell. A conjugate of formula III is susceptible to cleavage by pH less than or equal to 6.0, and the acid-catalyzed cleavage is accelerated by heating above room temperature, about 23° C. Since targeting molecules such as antibodies bind to cell surface receptors which are internalized into the cytoplasm via acidified compartments, it is believed that the release to the cytoplasm of an agent from a conjugate of the type described herein is the result of this transient exposure to acidic pH. Further, because warm-blooded animals such as man have normal body temperatures above 23° C., body heat may be a factor in the release. The delivery of an agent free of its targeting molecule carrier to the cytoplasm of a targeted cell increases its potency as compared to the agent when irreversibly linked to its carrier. This method is useful to diagnose, stage, evaluate or treat diseases such as cancer in humans.

A related aspect of the present invention provides methods for isolating compounds. The isolation of a compound, e.g., from a reaction mixture, is often a difficult and/or tedious process. It was widely believed that the attachment to a solid phase of a reagent with an affinity for a compound was the panacea for the problems with earlier isolation procedures.

In theory, the undesired compounds are removed simply by washing the solid phase. In practice, however, washing conditions sufficient to remove the impurities often result in removal of the compound of interest. This is due to the fact that the compound is only held to the solid phase by noncovalent interactions with the reagent. While covalent attachment of the compound to the solid phase is preferable from a washing standpoint, it can make recovery of the compound off the solid phase impossible. The method of the present invention provides a way to attach covalently a compound of interest and thereby facilitate removal of undesired compounds, yet nevertheless permit easy recovery of the compound of interest from the solid phase.

Within the present invention, one embodiment of a method for isolating compounds is directed to compounds containing an available nucleophilic group, such as a free sulfhydryl, free amino or free hydroxyl group, and comprises the following steps. To a solid phase is conjugated a reagent having the formula (I):

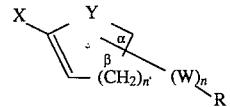

to form a derivatized solid phase. The derivatized solid phase is contacted with a sample solution in which a compound containing an available nucleophilic group is present, such that the compound binds to the derivatized solid phase, thereby removing the compound from the sample solution. The compound bound to the derivatized solid phase may be released.

The elements of the reagent depicted above in formula I include the following: W, n, Y, n', $\alpha$, $\beta$, and X which are defined above. R is a chemically reactive moiety which may be a nucleophile or an electrophile. When the solid phase contains available nucleophilic groups, such as a free amino group, R is an electrophile such as an activated ester. Conversely, when the solid phase contains electrophilic groups, R is a nucleophile. Examples of suitable solid phases include controlled pore glass and preformed polymers, such as polyvinyls, polyacrylamides, polydextrans, and polystyrenes.

The step of conjugating the reagent to the solid phase attaches the former to the latter via R, thereby forming a derivatized solid phase. A sample solution, in which a compound containing an available nucleophilic group is present, is contacted with the derivatized solid phase.

Examples of available nucleophilic groups include free sulfhydryl, free amino, and free hydroxyl groups. The step of contacting results in covalent attachment of the compound to the derivatized solid phase via addition to the carbon-carbon double bond on the reagent's ring. Following the step of contacting, it may be desirable to wash the solid phase to remove noncovalently bound compounds.

The covalently bound compound may be released in native form from the solid phase by a variety of ways. For example, cleavage of the bond formed between the compound and a ring-carbon of the derivatized solid phase may be achieved by mildly acidic conditions or divalent cations, and be accelerated by heat. In particular, cleavage occurs by decreasing the pH of a solution contacting the solid phase to 6.0 or lower, by adding divalent cations such as $Zn^{2+}$ at a concentration at least equimolar to that of the reagent attached to the solid phase, or by raising the temperature above 23° C. in the presence of pH 6.0 or lower.

Alternatively, an undesired compound or compounds, rather than a compound of interest, may contain an available nucleophilic group. In this situation, the undesired compound or compounds will bind to a derivatized solid phase and the compound of interest will not bind. Therefore, the method may be used to purify by a single technique one or more compounds from a reaction mixture so long as the compounds of interest or the impurities, but not both, contain available nucleophilic groups.

Another way to use this type of reagent to isolate a compound is to bind the compound to the reagent before contacting with a solid phase. For example, a sample solution in which a compound containing an available nucleophilic group, such as a free sulfhydryl, free amino, or free hydroxyl group, is present, may be reacted with a reagent whose general structure is as described above. The step of reacting results in covalent attachment of the reagent to the compound via addition to the carbon-carbon double bond on the reagent's ring. A reaction mixture is thereby formed, wherein a derivatized compound is present. The reaction mixture is then contacted with a solid phase capable of selectively binding, covalently or noncovalently, the derivatized compound, thereby removing the derivatized compound from the reaction mixture. The bound compound may be released in native form by a variety of ways, including those described above.

Within the present invention, another embodiment of a method for isolating compounds is directed to compounds containing a group capable of reacting with a chemically reactive group and comprises the following steps. To a solid phase is conjugated, via R, a reagent having the formula (IV):

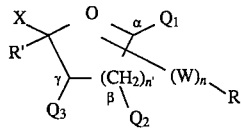

to form a derivatized solid phase. The derivatized solid phase is contacted with a sample solution in which a compound containing a group capable of reacting with R' is present, such that the compound binds to the derivatized solid phase, thereby removing the compound from the sample solution. The compound bound to the derivatized solid phase may be released.

The elements of the reagent depicted above in formula IV include the following: R', W, n, $Q_{1-3}$, n', α, β, γ, X and R, which are defined above. R' is a chemically reactive moiety and may be a nucleophile or an electrophile. The selection is generally determined by whether the reactive group on a compound is nucleophilic or electrophilic.

R is a chemically reactive moiety which may be a nucleophile or an electrophile. When the solid phase contains available nucleophilic groups, such as a free amino group, R is an electrophile such as an activated ester. Conversely, when the solid phase contains electrophilic groups, R is a nucleophile. Examples of suitable solid phases include controlled pore glass and preformed polymers, such as polyvinyls, polyacrylamides, polydextrans, and polystyrenes.

The step of conjugating the reagent to the solid phase attaches the former to the latter via R, thereby forming a derivatized solid phase. The above discussion regarding R and R' is applicable here as well. A sample solution, in which a compound containing a group capable of reacting with R' is present, is contacted with the derivatized solid phase. Reactions of a compound with R' of a reagent include both attachment of the compound to the reagent with R' (or its reaction product) interposed, as well as attachment of the compound directly to a ring-carbon of the reagent with R' having been displaced. The step of contacting results in covalent attachment of the compound to the derivatized solid phase. Following the step of contacting, it may be desirable to wash the solid phase to remove noncovalently bound compounds.

The covalently bound compound may be released from the solid phase by a variety of ways. For example, cleavage of the bond formed between a heteroatom and the ring-carbon, which bore R', of the derivatized solid phase may be achieved by mildly acidic conditions and be accelerated by heat. In particular, cleavage occurs by decreasing the pH of a solution contacting the solid phase to 6.0 or lower or by raising the temperature above 23° C. in the presence of pH 6.0 or lower.

Alternatively, an undesired compound or compounds, rather than a compound of interest, may contain a group capable of reacting with R'. In this situation, the undesired compound or compounds will bind to a derivatized solid phase and the compound of interest will not bind. Therefore, the method may be used to purify by a single technique one or more compounds from a reaction mixture so long as the compounds of interest or the impurities, but not both, contain groups capable of reacting with R'.

Another way to use this type of reagent to isolate a compound is to bind the compound to the reagent before contacting with a solid phase. For example, a sample solution in which a compound containing a group capable of reacting with R' is present may be reacted with a reagent whose structure is as described above. The step of reacting results in covalent attachment of the reagent to the compound. A reaction mixture is thereby formed wherein a derivatized compound is present. The reaction mixture is then contacted with a solid phase capable of selectively binding, covalently or noncovalently, the derivatized compound, thereby removing the derivatized compound from the reactive mixture. The bound compound may be released in native form by a variety of ways, including those described above.

Yet another aspect of the present invention includes methods for introducing into a compound a free sulfhydryl, free amino, or free hydroxyl group. The two reagents widely used for the introduction of —SH groups in proteins are S-acetyl mercaptoacetic acid succinimidate ester (SATA) and mercaptoacetyl succinic anhydride (SAMSA). In both cases, the antibody (Ab) reacts to form an amide bond. In the case of SATA, the antibody after the reaction is stored as Ab-Lys-NH—COCH$_2$—SCOCH$_3$ at −20° C. from which free sulfhydryl (—SH) groups are generated by treatment with hydroxylamine. In the case of SAMSA, the amine from the protein reacts with the anhydride to form Ab-LYs-NHCO—CH$_2$—CH(SH)—COOH. Both reagents suffer from several disadvantages. First, the S-acetyl protecting group is base labile, i.e., can be hydrolyzed at pH 7–8. Ideally that is the pH necessary for the conjugation of antibody with electrophiles. Hydrolysis of thioacetyl groups effectively competes with displacement reactions. Second, thioesters are by themselves active esters. Amines will react with thioesters to give N-acetyl compounds. Third, in the case of mercaptoacetyl succinic anhydride, reaction of Fab gives several components including aggregates. This results directly from competing reactions of the proteins with the reagents. The methods of the present invention overcome the above problems and, furthermore, reagents like hydroxylamine need not be used to generate the free —SH group.

Within the present invention, one embodiment of a method for introducing into a compound a free —SH, —NH$_2$, or —OH group comprises the steps of reacting a compound with a reagent having the formula (V):

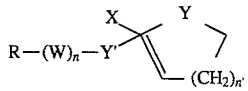

to form a reagent-linked compound and cleaving the reagent-linked compound at the bond between Y' and the ring, thereby introducing into the compound a free sulfhydryl, free amino, or free hydroxyl group, depending upon whether Y' is S, N, or O, respectively.

The elements of the reagent depicted above in formula V include the following: W, n, Y, n', and X, which are defined above for formula I. Y' is a heteroatom. Preferred heteroatoms include sulfur (S), oxygen (O), or nitrogen (N). R is a chemically reactive moiety. The moiety may be a nucleophile or an electrophile. The selection is generally determined by whether the reactive group on a compound is nucleophilic or electrophilic. For example, where the reactive group on a compound is a nucleophile, such as an amino group, R is an electrophile such as an activated ester or an anhydride. An exception to this method of selecting R is where it is desired to form a disulfide bond between a compound and R. In that situation, a sulfhydryl group on the compound and a sulfhydryl group on the reagent, i.e., R is —SH, may be oxidized to form a disulfide bond. Because disulfide linkages are cleavable, e.g., by reducing agents, it is possible to create a reversibly modified compound. For example, where Y' is N and R is —SH and the reagent and a compound are joined by a disulfide bond, the result is the addition to a compound of an amino group that can be removed.

Any compound containing a functional group capable of reacting with the reagent via R may be employed in the present invention. The functional group may be present on a native form of a compound or be added to it. Preferred compounds are proteins generally, e.g., antibodies.

When the compound is reacted with the reagent, the former is attached to the latter via R, thereby forming a reagent-linked compound. The reagent-linked compound is then cleaved at the bond between Y' and a ring carbon, thereby forming compounds with free sulfhydryl, free amino, or free hydroxyl groups, depending upon whether Y' is an S, N, or O, respectively. The step of cleaving may be achieved by a variety of ways, including exposing the reagent-linked compound to mildly acidic conditions, heat, or divalent cations. In particular, cleavage occurs by decreasing the pH to 6.0 or lower, by adding divalent cations such as Zn$^{2+}$ at a concentration at lease equimolar with the reagent-linked compound, or by raising the temperature to at least 37° C. in the presence of pH 6.0 or lower. The preferred pH range is 5.0–6.0.

The step of cleaving results in Y' remaining attached to the compound. Therefore, introduction of a desired free heteroatom into a compound is achieved by selection of the appropriate heteroatom for Y'. For example, if the addition of a free amino group to a compound is desired, then the heteroatom selected for Y' is N.

A preferred use of the method with proteins is to introduce a free sulfhydryl group. For example, an amino group of a protein, e.g., a lysine residue, may be used as the nucleophilic group to react with a form of the reagent where Y' is S. When the resulting reagent-linked protein is cleaved, the net effect is to convert a free amino group on the protein to a free sulfhydryl group. Another preferred use is to introduce an amino group.

Within the present invention, another embodiment of a method for introducing into a compound a free —SH, free —NH$_2$, or free —OH group comprises the steps of reacting a compound with a reagent having the formula (VI):

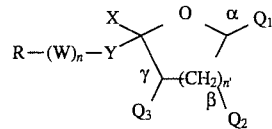

to form a reagent-linked compound and cleaving the reagent-linked compound at the bond between Y and the ring, thereby introducing into the compound a free sulfhydryl, free amino, or free hydroxyl group, depending upon whether Y is S, N, or O, respectively.

The elements of the reagent depicted above in formula VI include the following: W, n, $Q_{1-3}$, n', and X, which are defined above for formula III. Y is a heteroatom. Preferred heteroatoms include sulfur (S), oxygen (O), or nitrogen (N). R is a chemically reactive group. The group may be a nucleophile or an electrophile. The selection is generally determined by whether the reactive group on a compound is nucleophilic or electrophilic. For example, where the reactive group on a compound is a nucleophile, such as an amino group, R is an electrophile such as an activated ester or an anhydride. An exception to this method of selecting R is where it is desired to form a disulfide bond between a compound and R. In that situation, a sulfhydryl group on the compound and a sulfhydryl group on the reagent, i.e., R is —SH, may be oxidized to form a disulfide bond. Because disulfide linkages are cleavable, e.g., by reducing agents, it is possible to create a reversibly modified compound. For example, where Y is N and R is —SH and the reagent and a compound are joined by a disulfide bond, the result is the addition to a compound of an amino group that can be removed.

Any compound containing a functional group capable of reacting with the reagent via R may be employed in the present invention. The functional group may be present on a native form of a compound or be added to it. Preferred compounds are drugs and proteins generally, e.g., antibodies.

When the compound is reacted with the reagent, the former is attached to the latter via R, thereby forming a reagent-linked compound. The reagent-linked compound is then cleaved at the bond between Y and a ring carbon, thereby forming compounds with free sulfhydryl, free amino, or free hydroxyl groups, depending upon whether Y is an S, N, or O, respectively. The step of cleaving may be achieved by a variety of ways, including exposing the reagent-linked compound to mildly acidic conditions, heat, or divalent cations. In particular, cleavage occurs by decreasing the pH to 6.0 or lower or by raising the temperature to at least 37° C. in the presence of pH 6.0 or lower. The preferred pH range is 5.0–6.0.

The step of cleaving results in Y remaining attached to the compound. Therefore, introduction of a desired free heteroatom into a compound is achieved by selection of the appropriated heteroatom for Y. For example, if the addition of a free amino group to a compound is desired, then the heteroatom selected for Y is N.

A preferred use of the method with proteins is to introduce a free sulfhydryl group. For example, an amino group of a protein, e.g., a lysine residue, may be used as the nucleophilic group to react with a form of the reagent where Y is S. When the resulting reagent-linked protein is cleaved, the net effect is to convert a free amino group on the protein to a free sulfhydryl group. Another preferred use is to introduce an amino group.

To summarize the examples which follow, Example I provides the preparation of cleavable immunoconjugates utilizing 6-mercaptopurine and MAb 9.2.27. Example II describes testing for the in vitro cytotoxicity and the biodistribution and toxicology of the cleavable immunoconjugates utilizing Pseudomonas exotoxin. Example III discloses isolation of phenylmercaptoacetamide utilizing a derivatized agarose. Example IV describes the introduction of a free sulfhydryl group into intact MAb 9.2.27. Example V provides the preparation of cleavable conjugates utilizing MAb 9.2.27 and ethiophos, melphalan or adriamycin. Example VI describes an in vitro assay and the biodistribution and toxicology of the cleavable conjugates utilizing adriamycin. Example VII discloses isolation of an amine utilizing a glucoronide and a derivatized agarose. Example VIII describes the introduction of a free amino group into intact MAb 9.2.27.

The following examples are offered by way of illustration and not by way of limitation.

EXAMPLES

EXAMPLE I

Preparation of Cleavable Immunoconjugates

A. Preparation of a Derivatized Agent

The derivatized agent having the following formula is prepared as described below:

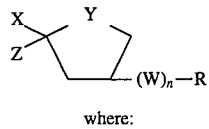

where:

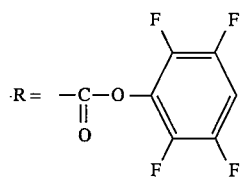

W=—CH$_2$— n=1
Y=oxygen
X=CH$_3$
Z=6-mercaptopurine

1. Preparation of 2,3-dihydro-5-methyl-furan-3-yl acetic acid 1.

Compound 1 where n'=1 is synthesized according to the procedure described by D. V. Banthorpe et al. (*Phytochemistry* 18:666–667, 1979) as depicted in Scheme I.

Scheme I

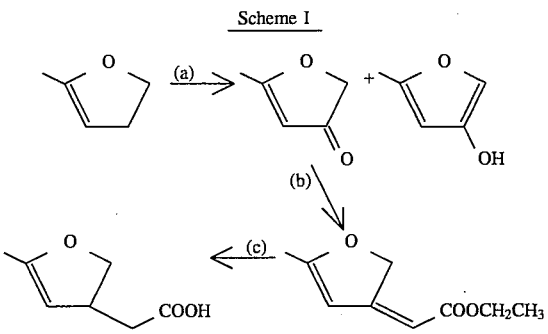

(a) SeO$_2$, dioxane
(b) CH$_3$CH$_2$OOCH=PO$_3$
(c) Raney nickel

Similarly, the dihydropyran derivative 1B where n'=2 is prepared using the analogous method described in Scheme I.

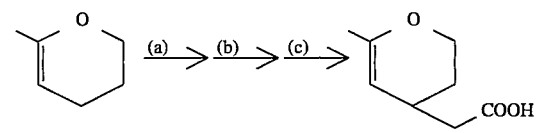

2. Reaction of an Agent with Compound 1.

A hemithioketal derivative, 2, of 6-mercaptopurine, an anti-tumor drug, where n'=1 is prepared according to the pathway depicted in Scheme II below. Specifically, a mixture of 2,3-dihydro-5-methylfuran-3-yl acetic acid 1 (1.0 equivalent) and 6-mercaptopurine (1.0 equivalent) in THF is treated with a catalytic amount of para-toluene sulfonic acid (0.01 equivalent). The resultant mixture is allowed to stir at room temperature overnight. The organic phase is washed with H$_2$O and dried over anhydrous MgSO$_4$. After removal of the solvent, a hemithioketal derivative of 6-mercaptopurine, product 2, is obtained.

Scheme II

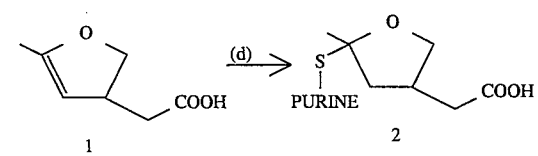

(d) 6-mercaptopurine, pTsOH, THF

3. Conversion of 2 to the tetrafluorophenyl ester 3.

An activated ester form, 3, of 2 is prepared according to the pathway depicted in Scheme III below. Specifically, the hemithioketal derivative of 6-mercaptopurine, 2 (1.0 equivalent) is combined with 2, 3, 5, 6 tetrafluorophenol (TFP) (1.1 equivalent) in anhydrous TFH. After addition of crystalline dicyclohexyl carbodiimide (DCC) (1.1 equivalent), the mixture is stirred for 12 hours at 25° C. After removal of the precipitated dicyclohexyl urea by filtration and removal of the THF under reduced pressure, the product is obtained. After chromatography on silica gel, product 3 is obtained.

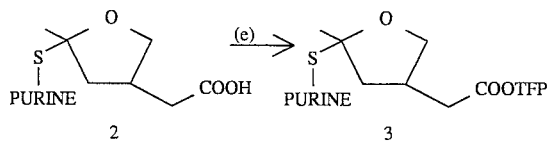

(e) 2,3,5,6-tetrafluorophenol, DDC, THF

B. Conjugation of TFP ester 3 with Monoclonal Antibody 9.2.27

The monoclonal antibody 9.2.27 is directed to a melanoma-associated antigen and is prepared according to Morgan et al., *Hybridoma* 1:27–35, 1981. A methanolic solution of 3 (25 μl total volume) is transferred to a vial containing buffered antibody solution (pH 8.5–10) of at least 1 mg antibody per 1 ml. The conjugation mixture is warmed at 37° C. for 20 minutes. The modified antibody is purified either using gel permeation chromatography or small pore filtration (e.g., Centricon ultra centrifugation).

EXAMPLE II

A. In Vitro Cytotoxicity of Cleavable Immunoconjugates

Cleavable immunoconjugates, where Pseudomonas exotoxin (PE) is the agent, are prepared in accordance with a modification of the procedures of Example 1.

Prior to reaction with compound 1 (Example I.A.2), the carboxyl groups on PE are protected, e.g., by suspension of PE in 0.1N methanolic HCl at room temperature overnight. PE is then treated with a reducing agent to provide a free sulfhydryl for reaction with compound 1. A mixture of compound 1 (1.0 equivalent) and PE (1.0 equivalent) in an aqueous solution containing 10% dioxane is treated with a catalytic amount of para-toluene sulfonic acid (0.01 equivalent). The resultant mixture is allowed to stir at room temperature overnight and the derivatized PE is isolated by gel filtration chromatography. The succinimidyl ester of derivatized PE is prepared using N-hydroxysuccinimide and a water soluble carbodiimide. After separation by gel filtration chromatography, the carboxyl groups on PE are deblocked, e.g., by hydroxylamine, and PE is conjugated to MAb 9.2.27 according to Example I.B.

ADP-ribosylation is measured in a cell-free system according to the method of B. G. Vanness et al., *J. Biol. Chem.* 255:10717 (1980). The ADP-ribosylation activity of the cleavable PE immunoconjugates in the presence and absence of dilute acid or divalent cations is compared to the activities under the same conditions of PE alone and of non-cleavable PE immunoconjugates.

In vitro cytoxicity testing is performed according to the method of A. C. Morgan, Jr. et al., *JNCI* 78:1101, 1987, using $^3$H-leucine incorporation to measure protein synthesis inhibition due to ADP-ribosylation activity by PE. For testing of PE:9.2.27 conjugates, two human melanoma cell lines are utilized as targets—A375 met mix (antigen-positive) and A375 I° Primary (antigen-negative). For assay of PE:anti-TAC conjugates, target cells are HUT 102 (antigen-positive) and CEM (antigen-negative) as discussed in D. J. P. Fitzgerald et al., *J. Clin. Invest*, 74:966, 1984. Conjugates are examined in two formats: (a) short exposure, wherein the conjugate is incubated with target cells for one hour at 37° C., the monolayer gently washed, and the cultures continued for up to 72 hours before the addition of $^3$H-leucine; and (b) long exposure, wherein the conjugate is added and the target cells exposed for the entire length of the culture period.

B. Biodistribution and Toxicology of Cleavable Immunoconjugates

Tumor localization and biodistribution of conjugates are examined in a nude mouse xenograft model of human melanoma, according to the method of K. M. Hwang et al., *Canc. Res.* 450:4150 (1986). PE is radiolabeled with $^{125}$I-para-iodophenyl (PIP) as shown by D. S. Wilbur et al., *J. Nucl. Med.* 27:959 (1986). This radiolabel is not subject to dehalogenation, and thereby can be used to more effectively follow the biodistribution of conjugates. The radiolabeled PE is conjugated to a monoclonal antibody, such as 9.2.27 or anti-TAC, using the linkers of the present invention as described in Example I. Animals are sacrificed at 20 hours post-injection, and organs are blotted, weighed and counted. A % dose per gram is calculated for each tissue. In addition, serum half-life is estimated by retroorbital sampling of whole blood.

Mice are administered different doses of PE-anti-TAC and PE:9.2.27 conjugates intraperitoneally to determine an $LD_{100}$. Following administration of radiolabeled PE immunoconjugates, the resultant tumor localization and biodistribution of the conjugates are determined. Non-specific toxicity of PE:anti-TAC conjugates is also assessed in cynomolgus monkeys. Monkeys are monitored for liver enzyme levels, and are observed for other relevant symptoms, including appetite, presence/absence of nausea, and temperature.

EXAMPLE III

Isolation of a Compound Containing Available Nucleophilic Group by a Derivatized Solid Phase A. Preparation of a Derivatized Solid Phase 1. Synthesis of Reagent, 4, for Derivatization of Solid Phase.

Compound 1, 2,3-dihydro-5-methyl-furan-3-yl acetic acid, is synthesized as described in Example I. To a solution of 1, (1.0 equivalent) in dry dimethylforamide (DMF) is added crystalline dicyclohexyl carbodiimide (DCC) (1.1 equivalent), followed by the addition of N-hydroxysulfosuccinimidate (1.1 equivalent). After stirring at room temperature for 12 hours, the precipitated dicyclohexylurea (DCU) is removed by gravity filtration. The DMF is removed under reduced pressure and the resultant residue is dissolved in a minimal amount of 50:50 acetonitrite-H$_2$O. This compound 4 is then purified using silica gel chromatography.

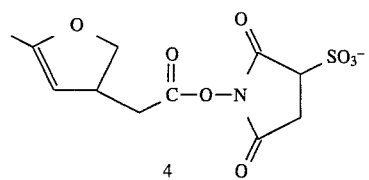

2. Coupling of 4 with AH-Sepharose-4B

Aminohexyl (AH)-Sepharose-4B is obtained from Pharmacia and swelling and washing of the gel is carried out according to the procedure in *Affinity Chromatography—Principles and Methods,* Pharmacia Publication, June 1979, pp. 22–23.

The above sulfosuccinimidate 4 is dissolved in bicarbonate buffer (pH=8) containing 5–10% acetonitrile at a concentration in excess of the spacer groups. The solution is added to the gel and pH is readjusted if necessary during the period of coupling, which is done overnight. The Sepharose-spacer-4 conjugate is stored at 4° C.

B. Isolation of Phenethylmercaptoacetamide with the Derivatized Solid Phase

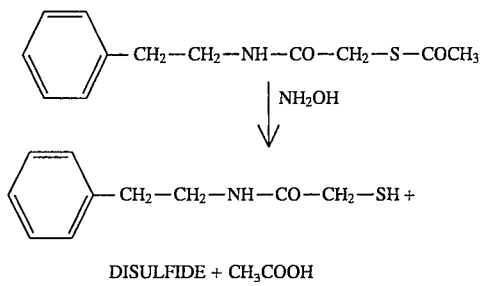

DISULFIDE + CH₃COOH

A solution of S-acetylphenethylthioacetamide is treated with excess hydroxylamine in methanol:water (1:1) to yield a mixture of products and unreacted starting material, as depicted above. The solution is passed through a column containing the derivatized Sepharose prepared in part A above. The thiol in the mixture (phenethylmercaptoacetamide) is retained in the column by formation of a covalent adduct, while the other compounds in the mixture (excess hydroxyl amine, the disulfide and unreacted S-acetylphenethylthioacetamide) are eluted.

The desired thiol is freed from the column by passing a pH 4–5 buffer through the column.

EXAMPLE IV

Introduction of a Free Sulfhydryl Group into an Antibody

A. Preparation of a Hemithioketal Derivative of Monoclonal Antibody. 9.2.27

1. Synthesis of a Hemithioketal.

A mixture of 2-methyl-4,5-dihydrofuran and 2-mercaptoacetic acid in THF are treated with a catalytic amount of para-toluene sulfonic acid according to the procedure in Example I.A.2. After removal of the solvent, S-(2-methyl-tetrahydrofuran-2-yl)mercaptoacetic acid is obtained. Alternatively, mercaptosuccinic acid is reacted with 2-methyl-4,5-dihydrofuran and then converted to a mercaptosuccinic anhydride derivative by a dehydrating agent such as dicyclohexyl carbodiimide.

The derivatized mercaptoacetic acid is converted to the tetrafluorophenyl (TFP) ester as described in Example I.A.3. Alternative active esters are formed by reaction with dicyclohexyl carbodiimide and N-hydroxysuccinimide or N-hydroxysulfosuccinimidate.

2. Conjugation of TFP ester to Monoclonal Antibody 9.2.27

Monoclonal antibody 9.2.27 is prepared according to the method described in Example I.B. A methanolic solution of an activated ester form of the mercaptoacetic acid derivative (25 μl total) is transferred to a vial containing a pH 8.0 buffered antibody solution. The antibody concentration is at least 1.0 mg/ml. The reaction mixture is incubated at 37° C. for 20 minutes. The derivatized antibody is purified using gel permeation chromatography or small pore filtration.

B. Generation of Free Sulfhydryl

The buffered solution of purified, derivatized 9.2.27 antibody is deoxygenated using a nitrogen sparge. The pH of the solution is then decreased to pH 5.0 using deoxygenated 0.1N HCl. The acidified antibody solution is kept at 5° C. to minimize sulfhydryl oxidation and is used within 30 minutes.

EXAMPLE V

Preparation of Cleavable Conjugates

A. Preparation of Derivatized Agents

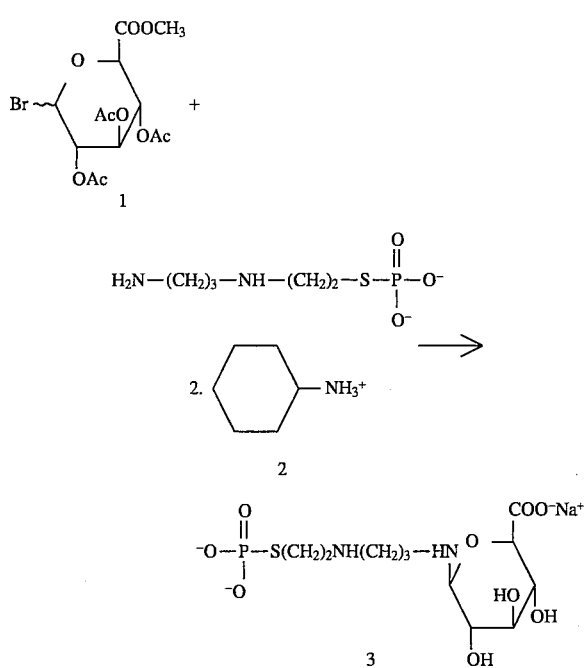

Preparation of 3: To a stirred solution of the glucoronide 1 (10 mmol) in absolute dioxane (100 mL) is added in portions a solution of bis-cyclohexylammonium salt of ethiophos 2 (10 mmol) in dioxane followed by triethylamine (1 eq.). The reaction mixture is refluxed for several hours. The insoluble part is filtered. The filtrate is diluted with water to opalescence, cooled in an ice-water bath, and ammonia gas is bubbled into it until saturation. The reaction mixture is stored at 0° C. overnight. Volatiles are evaporated in vacuo. The residue is diluted in methanol, a solution of sodium iodide in acetone is added, and then centrifuged to obtain 3 as a disodium salt. The disodium salt is converted to alkylammonium or pyridinium salt by passing through alkyl ammonium or pyridinium Dow-50 according to the procedure of D. B. Towbridge et al. (*J. Amer. Chem. Soc.* 94:3816, 1972).

Scheme 2

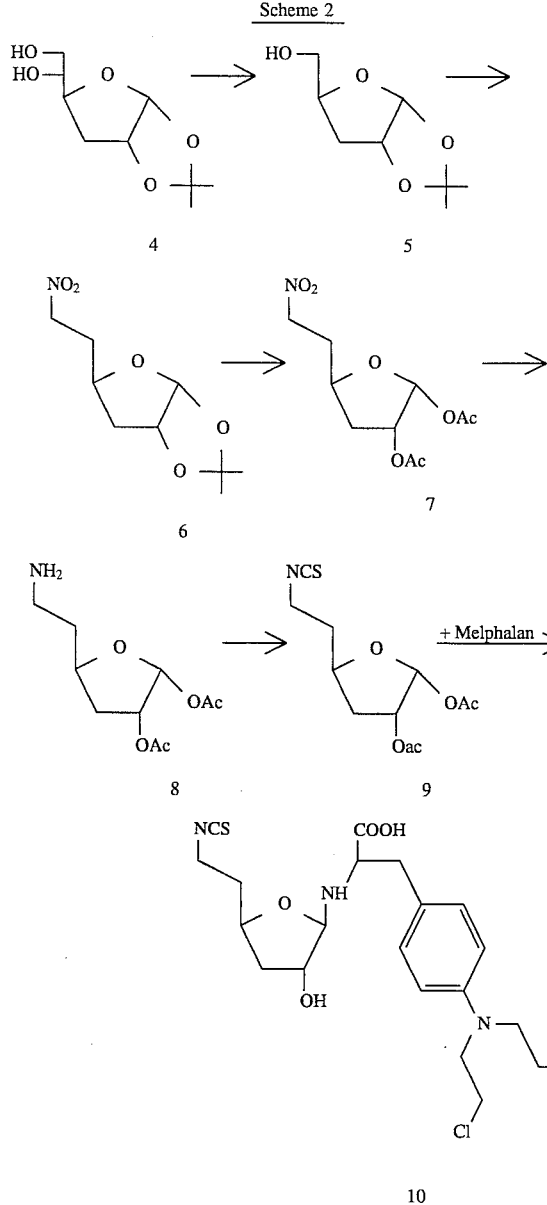

Preparation of 3,5-Dideoxy-5-isothiocyanatomethyl-1,2-di-O-acetyl-α-D-erythro-pentofuranoside 9:

i) 3-Deoxy-1,2-O-isopropylidine-α-D-erythropentofuranoside 5 is prepared from 4 according to the procedure of Murray and Prokop (D. H. Murray and J. Prokop in "Synthetic Procedures in Nucleic Acid Chemistry," edited by W. Zorbach and R. S. Tipson, Interscience Publishers, New York, 1968, pp. 193–197).

ii) The combined oxidation and nitroaldol condensation sequence (conversion of 5 to 6) is carried out according to Vrudhulas's modified procedures of Mock and Moffatt's methodology (V. M. Vrudhula, F. Kappler and A. Hampton, *J. Med. Chem.* 30:888, 1987, and G. A. Mock and J. G. Moffatt, *Nucleic Acids Res.* 10:6223, 1982). Conversion of the isopropylidine derivative 6 to the diacetyl derivative is accomplished using acetic anhydride-boron trifluoride in ether according to the procedure of S. Lesage and A. S. Perlin, *Can. J. Chem.* 56:2889, 1978.

iii) To a suspension of preproduced Adam's catalyst in methanol is added a solution of the nitroalkane 7 (100 mg of catalyst/1 g of the compound), and the reduction is carried out in a Paar hydrogenator at 45 psi for 20 hours. The catalyst is filtered through celite and evaporated in vacuo to give the amino sugar 8, which is converted to the isothiocyanate 9 according to the procedure of H. A. Staab and G. Walther, *Liebigs. Ann. Chem.* 657:104, 1962, using thiocarbonyldiimidazole.

Preparation 10: An equimolar mixture of melphalan and the isothiocyanate are fused at 145°–150° C., and the isolation of the product is carried out according to the method of T. Sato, "Synthetic Procedures in Nucleic Acid Chemistry," edited by W. Zorbach and R. S. Tipson, Interscience Publishers, New York, 1968, pp. 264–68.

Scheme 3

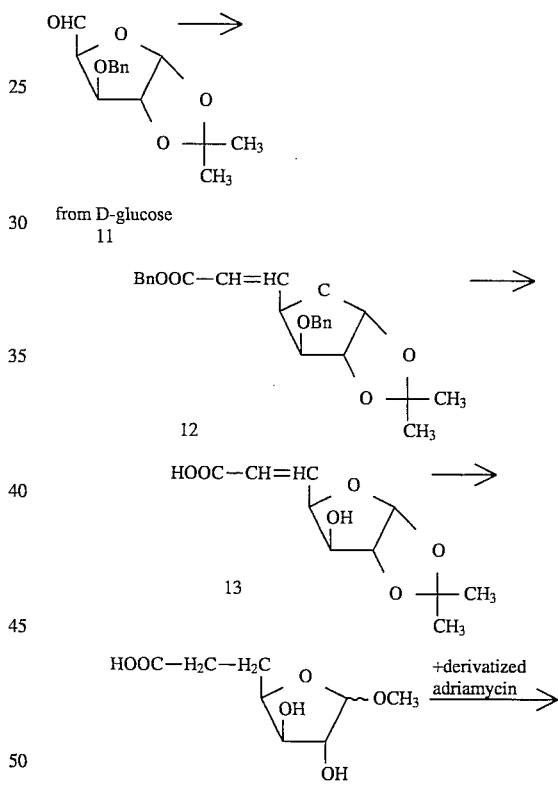

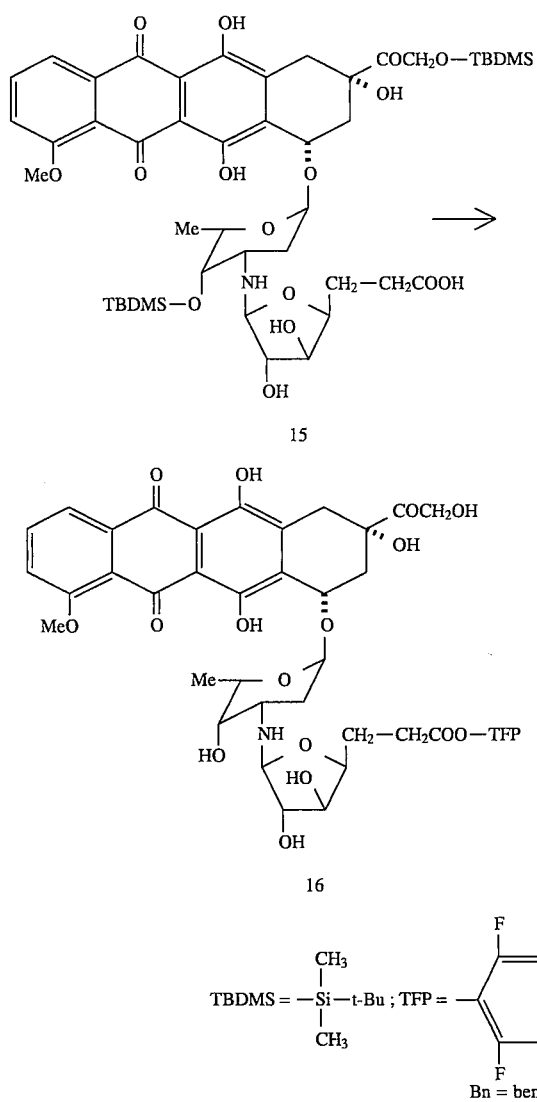

Preparation of 14:

i) The requisite starting material 11 is available according to the procedure of M. L. Wolform and S. Hanessian, *J. Org. Chem.* 27:1800, 1962, from D-glucose.

ii) The aldehyde 11 is reacted with BnOOC—CH=PPh$_3$ under Witting reaction conditions to the α,β-unsaturated ester 12.

iii) The benzylester 12 (1 mmol) is hydrogenated in methanol containing Pd—C (10%) (100 mg/mmol) in a Paar apparatus for 24 hours. At the end of the reaction, the catalyst is removed by filtration, and the filtrate containing 13 is again hydrogenated in the presence of 50 mg of Adam's catalyst to the saturated derivative. The catalyst is removed by filtration and the solvent is evaporated to give the product.

iv) The preceding product is stirred with 20 mL of 1% hydrogen chloride-methanol for 6 hours and evaporated to give methoxy sugar derivative 14.

Preparation of the disaccharide 15:

i) To a solution of 1 mmol of adriamycin in 2 mL of pyridine, 2.1 mmol of t-butyldimethylsilychloride is added, and the solution is stirred for 2–3 hours at room temperature. Pyridine is removed in vacuo, and the residue is chromatographed over silica gel to yield the bis-t-butyldimethylsilyl derivative.

ii) The silyl derivative of adriamycin (1 mmol) is fused with 14 and the product 15 is isolated in pure state by liquid chromatography.

Preparation of the active ester 16: The above acid is dissolved in 1:1 acetonitrile-water and an equimolar amount of 2,3,5,6-tetrafluorophenol is added, followed by 3–5 equivalents of 1-(3-diethylaminopropyl)-3-ethyl carbodiimide hydrochloride, and the mixture is stirred for 10–15 hours at room temperature. The solvents are removed in vacuo, and the product is isolated by liquid chromatography.

To a solution of the above compound in 5–10 mL of tetrahydrofuran, 2 mL (per mmol of the compound) of tetra-n-butyl ammonium fluoride is added and the solution is stirred for 1 hour. The active ester hydrochloride is isolated from the mixture by liquid chromatography.

B. Conjugation of TFP ester 16 with Monoclonal Antibody 9.2.27

The monoclonal antibody 9.2.27 is directed to a melanoma-associated antigen and is prepared according to Morgan et al., *Hybridoma* 1:27–35, 1981. An isopropanol solution of 16 (25 μl total volume) is transferred to a vial containing buffered antibody solution (pH 8.5–10) of at least 1 mg antibody per 1 ml. The conjugation mixture is warmed at 37° C. for 20 minutes. The modified antibody is purified either using gel permeation chromatography or small pore filtration (e.g., Centricon ultra centrifugation).

EXAMPLE VI

In Vitro Assay and Biodistribution With Cleavable Conjugates

A. In Vitro Assay for Drug Conjugates

1. Day 1: Cell Plating and Plate Setup.

(a) Growth of human carcinoma cells, raised in 10 DMEM.

(b) Cells are usually adherent lines and thus should be lifted with trypsin/EDTA. Cells should be passaged into microtiter plates at least 18–24 hours prior to the start of an assay.

(c) Count cells in hemocytometer. Cells should have a viability greater than 80% as measured by trypan blue exclusion.

(d) Cells are plated in 100 μl of DMEM at an appropriate concentration such that control wells will have just reached confluency by the end of the assay. For example, for the particular cell lines used, 3000 to 3500 cells per well is sufficient. Fill the outside rows of 96 well plates with sterile water to prevent evaporation.

(e) Incubate microtiter plates for a minimum of hours in a 37° C. humidified incubator before the addition of drugs and drug conjugates.

2. Day 2: Addition of Drugs and Drug Conjugates (a) Exact ID50 values may vary from cell line to cell line. It is well within the skill of an investigator of ordinary skill in this art to determine the appropriate dilution range of the samples to be tested. Usually the ID50 can be found within the range of 2000 nM to 0.2 nM for doxorubicin and 200 nM to 0.02 nM for doxorubicin conjugates for both the positive and negative cell lines for the antibody used.

(b) Set up 5 ml snap cap tubes in a test tube rack to make 5 serial 10-fold dilutions for each sample to be tested plus controls.

(c) Pipet 900 μl of medium to the last 4 tubes of dilution series. With the first tube, add the appropriate medium in order to start the dilution series at 2000 nM for doxorubicin and 200 nM for dox conjugates. Total volume of a tube should be 1000 μl.

(d) Add the appropriate amount of sample to the first tube of the dilution series. Mix by repetitive pipeting (approximately 5 times). Discard the pipet in the drug waste. Remove 100 μl of sample/medium from the first tube and place in tube number 2 of the dilution series. Mix by repetitive pipeting, and continue the procedure through the dilution sequence.

(e) Once all samples have been diluted, remove cells (that had been set up the previous day) from the incubator. For each dilution of the samples, place 100 μLl into the wells of the microtiter plate in triplicate on the positive and negative cell lines.

(f) Add 100 μl of medium to the control wells (wells without drug or conjugate sample added).

(g) Incubate the cells at 37° C. in a $CO_2$ humidified incubator for 18–24 hours.

(h) Once completed, dispense of waste material in drug refuse.

3. Day 3: Removal of Drugs from Plates (a) Remove the cells from the incubator.

(b) Gently remove sample/medium from all wells of 30 microtiter plate using a multichannel pipeter.

(c) Rinse the wells with PBS.

(d) Add 200 μl of medium per well.

(e) Place the plate into the incubator.

(f) Repeat procedure for other plates.

4. Day 5: MTT Assay (3-(4,5-dimethylthiaszol-2-yl)-2,5-diphenyl-2H-tetrazolium bromide)
Assay:

(a) A mixture of 50 μl of medium to 10 μL of MTT solution is used per well. Thus, for an entire plate of 60 wells, 3 mls of medium plus 600 μl of MTT solution is used. Mix the two prior to adding to cells.

(b) At this point of the assay, sterility is no longer a major precaution.

(c) The medium/MTT solution is removed from the wells.

(d) Add 60 μl of medium/MTT solution to each well.

(e) Incubate at 37° C. for cleavage of MTT to occur. Optimal times may vary with cell lines used, but 30 minutes is suitable for most purposes.

(f) After the 30 minute incubation, the medium/MTT solution is removed.

(g) After the medium/MTT is removed, add 100 μL of DMSO per well.

(h) Plates can be read immediately after addition of the DMSO.

(i) Tap the sides of the microtiter plate to ensure complete dissolving/mixing of the formazin crystals.

(j) Measure the absorbance on an ELISA plate reader. Use a test wavelength of 570 nm and reference wavelength of 630 nm. Also use the T/R setting on the Dynatech ELISA reader.

B. Biodistribution and Toxicology of Cleavable Conjugates

C-14-adriamycin (commercially available from Amersham Corporation, Illinois) is used to prepare compound 15 and compound 16 according to the procedure described in Scheme 3 (Example V). Compound 16 is conjugated to anti-melanoma antibody 9.2.27 according to the procedure in Example V.B.

Tumor localization and biodistribution of conjugates are examined in a nude mouse xenograft model of human melanoma, according to the method of K. M. Hwang et al., *Cancer Research,* 450:959, 1986. Animals are sacrificed at 20 hours post-injection and organs are blotted, weighed and counted. A percent dose per gram is calculated for each tissue. In addition, serum half-life is estimated by retroorbital sampling of whole blood.

Mice are administered different doses of drug-linker-anti-TAC and drug-linker-9.2.27 conjugates intraperitoneally to determine an $LD_{100}$. Following administration of C-14 adriamycin-linker-9.2.27 conjugates, the resultant tumor localization and biodistribution of the conjugates are determined. Nonspecific toxicity of drug-linker-TAC conjugates is also measured in cynomologous monkeys. Monkeys are monitored for liver enzyme levels and are observed for other relevant symptoms including loss of appetite, nausea and increased body temperature.

EXAMPLE VII

Isolation of an Amine-Containing Compound

A. Derivatization of an Amine in a Biological Fluid

A solution of a biological fluid containing an amine to be isolated is treated with the glucoronide shown in Scheme 1 (Example V) at pH 7–8. Using this procedure all the amines are converted to aminals. The biological fluid is adjusted to about pH=9–10 and the ester is converted to a sodium salt.

B. Coupling of the Above Acid to Hydroxymethyl Sepharose

Commercially available hydroxymethyl sepharose is washed and swelled according to the procedure described in Affinity Chromatography-Principles and Methods (Pharmacia) and stored in 4° C.

The above acid (from section A) is incubated with the solid phase pH 7.4 with 20–30 molar excess of EDCI (water-soluble carbodiimide). The coupling is done overnight to ensure all the derivatized amine is condensed with the hydroxyl groups (forming ester bonds). This method can be applied to aminohexyl sepharose also. In the latter case the aminals in the biological fluid is attached via the —COOH of the glucoronide as an amide. The conjugate thus prepared is stored at 4° C.

C. Isolation of Amine

The conjugate is loaded into a column and is washed several times with water and pH 7.4 buffer to remove other biological material. Finally the desired amine is isolated by passing pH 4–5 buffer through the column.

EXAMPLE VIII

Introduction of a Free $NH_2$ Group into an Antibody or Other Proteins

A. Preparation of an Aminals Derivative of Monoclonal Antibody 9.2.27

1. Synthesis of Protected Aminal.

A solution of tri-O-acetyl α-bromo-D-xylose in dry dioxane is treated with N-trifluoroacetylaminocaproic acid containing a 2 equimolar amount of triethylamine. The reaction mixture is refluxed for several hours. The insoluble part is filtered. The filtrate is evaporated and the residue is dissolved in methylene chloride and washed with water. The organic layer is dried over anhydrous sodium sulfate and evaporated to give the N-trifluoroacetyl aminal.

2. Conjugation of the Above Acid Above Acid with Monoclonal Antibody 9.2.27.

A solution of the antibody is prepared according to the method described in Example V.B. An isopropanol-water solution (isopropanol not to exceed 30%) of the above acid is transferred to a vial containing a pH 7.4 buffered antibody solution. The antibody concentration is at least 1.0 mg/mL. To this solution 10–15 equivalents of the above acid and 20–30 equivalents of EDCI (water-soluble carbodiimide) are added and the mixture is incubated at 37° C. for 2–3 hours. The derivatized antibody is isolated by gel permeation chromatography.

B. Removal of N-trifluoracetyl Group to Regenerate the Aminal

The above antibody solution is stirred with a 10% solution of aqueous piperidine (1 mL for approximately 1 mg of protein) for 10–15 hours at 0°–5° C. After treatment with piperidine, the protein is purified by passing over a PD-10 column. The protein obtained has the introduced amine group protected as an aminal.

C. Generation of Free Amines

The buffered solution of the above-protein is deoxygenated using a nitrogen purge. The pH of the solution is then decreased to pH 5.0–5.5 using 0.1N HCl. The acidified antibody is incubated at 37° C. for 1 hour to ensure complete removal of the xylose protecting moiety and complete generation of amino groups.

From the foregoing, it will be appreciated that, although specific embodiments of the invention have been described herein for purposes of illustration, various modifications may be made without deviating from the spirit and scope of the invention.

We claim:

1. A compound having the formula:

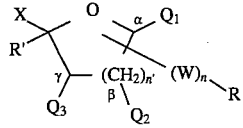

where:

R' is a chemically reactive group that is able to react directly with a diagnostically or therapeutically effective agent without activation of the group prior to conjugation with the agent;

W is a methylene, methylenoxy, or methylenecarbonyl group or combinations thereof;

n is 0 to 10;

$Q_1$, $Q_2$ and $Q_3$ are independently selected from H, OH, O-alkyl, and O-acyl, with the proviso that $Q_1$, $Q_2$ and $Q_3$ are not all H;

n' is 1 to 2;

X is H, an alkyl group of $C_6$ or less, or alkoxy group of $C_6$ or less; and

R is a chemically reactive group that is able to react directly with a targeting molecule without activation of the group prior to conjugation with the targeting molecule, with the provisos that R is attached directly or indirectly to one of the carbons designated α, β or γ, that when R is attached to α then $Q_1$ is H, that when R is attached to β then $Q_2$ is H, that when R is attached to γ then $Q_3$ is H, and that R and R' are not the same.

2. A compound having the formula:

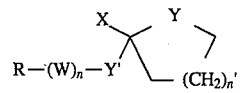

where:

R is a chemically reactive group that is able to react directly without activation of the group prior to conjugation with a molecule;

W is a methylene, methylenoxy, or methylenecarbonyl group or combinations thereof;

n is 0 to 30;

Y' is S, N, or O;

X is H, alkyl group of $C_6$ or less, or alkoxy group of $C_6$ or less;

n' is 1 to 2; and

Y is an O, S or NR', wherein R' is an alkyl group of $C_6$ or less.

3. A compound having the formula:

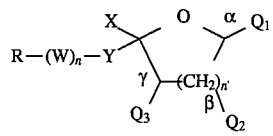

where:

R is a chemically reactive group that is able to react directly without activation of the group prior to conjugation with a molecule;

W is a methylene, methylenoxy, or methylenecarbonyl group or combinations thereof;

n is 0 to 30;

Y is S, N, or O;

X is H, alkyl group of $C_6$ or less, or alkoxy group of $C_6$ or less;

n' is 1 to 2; and $Q_1$, $Q_2$ and $Q_3$ are independently selected from H, OH, O-alkyl, O-acyl, and derivatives thereof, with the proviso that $Q_1$, $Q_2$ and $Q_3$ are not all H.

* * * * *